(12) United States Patent
Wojcicki et al.

(10) Patent No.: US 8,543,339 B2
(45) Date of Patent: Sep. 24, 2013

(54) GAMETE DONOR SELECTION BASED ON GENETIC CALCULATIONS

(75) Inventors: Anne Wojcicki, Palo Alto, CA (US); Linda Avey, Lafayette, CA (US); Joanna Louise Mountain, Menlo Park, CA (US); John Michael Macpherson, Palo Alto, CA (US); Joyce Yeh-hong Tung, Menlo Park, CA (US)

(73) Assignee: 23andMe, Inc., Mountain View, CA (US)

( * ) Notice: Subject to any disclaimer, the term of this patent is extended or adjusted under 35 U.S.C. 154(b) by 347 days.

(21) Appl. No.: 12/592,950

(22) Filed: Dec. 4, 2009

(65) Prior Publication Data

US 2010/0145981 A1   Jun. 10, 2010

Related U.S. Application Data

(60) Provisional application No. 61/201,101, filed on Dec. 5, 2008.

(51) Int. Cl.
*G06F 7/00* (2006.01)
(52) U.S. Cl.
USPC .................. 702/19; 702/20; 703/13; 707/700

(58) Field of Classification Search
None
See application file for complete search history.

(56) References Cited

U.S. PATENT DOCUMENTS

| | | | |
|---|---|---|---|
| 6,844,156 B2 * | 1/2005 | Rosen ........................... | 435/6.18 |
| 7,599,802 B2 * | 10/2009 | Harwood et al. ............... | 702/20 |
| 7,668,658 B2 * | 2/2010 | Koster et al. .................... | 702/19 |
| 2005/0278125 A1 * | 12/2005 | Harwood et al. ............... | 702/20 |
| 2006/0008859 A1 * | 1/2006 | Seul et al. ...................... | 435/7.25 |
| 2006/0205001 A1 * | 9/2006 | Zhang et al. ....................... | 435/6 |
| 2007/0042369 A1 | 2/2007 | Reese et al. | |
| 2007/0093968 A1 * | 4/2007 | Zhang et al. .................... | 702/19 |
| 2009/0299645 A1 * | 12/2009 | Colby et al. .................... | 702/19 |
| 2010/0022406 A1 * | 1/2010 | Srinivasan et al. ................ | 506/9 |
| 2010/0191735 A1 * | 7/2010 | Reiss et al. ..................... | 707/740 |
| 2011/0124515 A1 * | 5/2011 | Silver ................................ | 506/8 |
| 2012/0078901 A1 * | 3/2012 | Conde ........................... | 707/736 |

* cited by examiner

*Primary Examiner* — Mary Zeman

(74) *Attorney, Agent, or Firm* — Van Pelt, Yi & James LLP

(57) ABSTRACT

Gamete donor selection includes receiving a specification including a phenotype of interest, receiving a genotype of a recipient and a plurality of genotypes of a respective plurality of donors, determining statistical information pertaining to the phenotype of interest based at least in part on different pairings of the genotype of the recipient and a genotype of a donor in the plurality of donors, and identifying a preferred donor among the plurality of donors, based at least in part on the statistical information determined.

28 Claims, 7 Drawing Sheets

I Prefer a Child with:

| Low Risk of ▼ | | Colorectal Cancer ▼ | |
|---|---|---|---|
| Low Risk of | ☐ | Colorectal Cancer | ☐ |
| High Probability of | | Congenital Heart Defects | |
| | | Breast Cancer | |
| | | ... | |

=

| Low Risk of ▼ | | Congenital Heart Defects ▼ | |
|---|---|---|---|
| Low Risk of | ☐ | Colorectal Cancer | |
| High Probability of | | Congenital Heart Defects | ☐ |
| | | Breast Cancer | |
| | | ... | |

>

| High Probability of ▼ | | Green Eyes ▼ | |
|---|---|---|---|
| Low Risk of | | Blue Eyes | |
| High Probability of | ☐ | Brown Eyes | |
| | | Can Taste Bitter | |
| | | Cannot Taste Bitter | |
| | | ... | |

Preferred Donors:

| Donor | Score | Colorectal Cancer | Congenital Heart Defects | Green Eyes |
|---|---|---|---|---|
| A | 80 | 0.01% | 0.005% | 65% |
| B | 72 | 0.015% | 0.006% | 70% |
| C | 60 | 0.02% | 0.006% | 50% |

FIG. 4

I Prefer a Child with:

⊙ Longest Expected Life Span
○ Least Expected Life Cost of Health Care
○ Least Expected Cumulative Duration of Hospitalization

Preferred Donors:

| Donor | Expected Life Span |
|---|---|
| X | 90 |
| Y | 87 |
| Z | 82 |

FIG. 5

GAMETE DONOR SELECTION BASED ON GENETIC CALCULATIONS

CROSS REFERENCE TO OTHER APPLICATIONS

This application claims priority to U.S. Provisional Patent Application No. 61/201,101 entitled INHERITANCE CALCULATOR filed Dec. 5, 2008 which is incorporated herein by reference for all purposes.

BACKGROUND OF THE INVENTION

Gamete storage facilities such as sperm/egg banks have increasingly enabled people to have greater control and more choices in reproduction. Presently, some facilities collect sperm or egg donations as well as certain profile information pertaining to the donors. Such information typically includes the donor's race, height, weight, age, blood type, health condition, eye color, educational background, family history, etc. A potential recipient can review the profiles and make a selection. Although the personal profiles of the donors can serve a useful purpose for the potential recipient to make a more informed choice, such information typically offers only limited insight for recipients with specific concerns about certain genetic traits, such as inherited diseases, to make a truly informed choice. For example, a recipient with a family history of breast cancer may be concerned about receiving a donation from someone who is also in a high risk group; however, if the family history information is incomplete or unavailable, the recipient would not be able to make an informed choice.

BRIEF DESCRIPTION OF THE DRAWINGS

Various embodiments of the invention are disclosed in the following detailed description and the accompanying drawings.

FIG. 4 is a diagram illustrating an embodiment of a user interface for making user specification and displaying the results.

FIG. 5 is a user interface diagram illustrating another embodiment of a user interface that displays the results.

DETAILED DESCRIPTION

Figure 1:
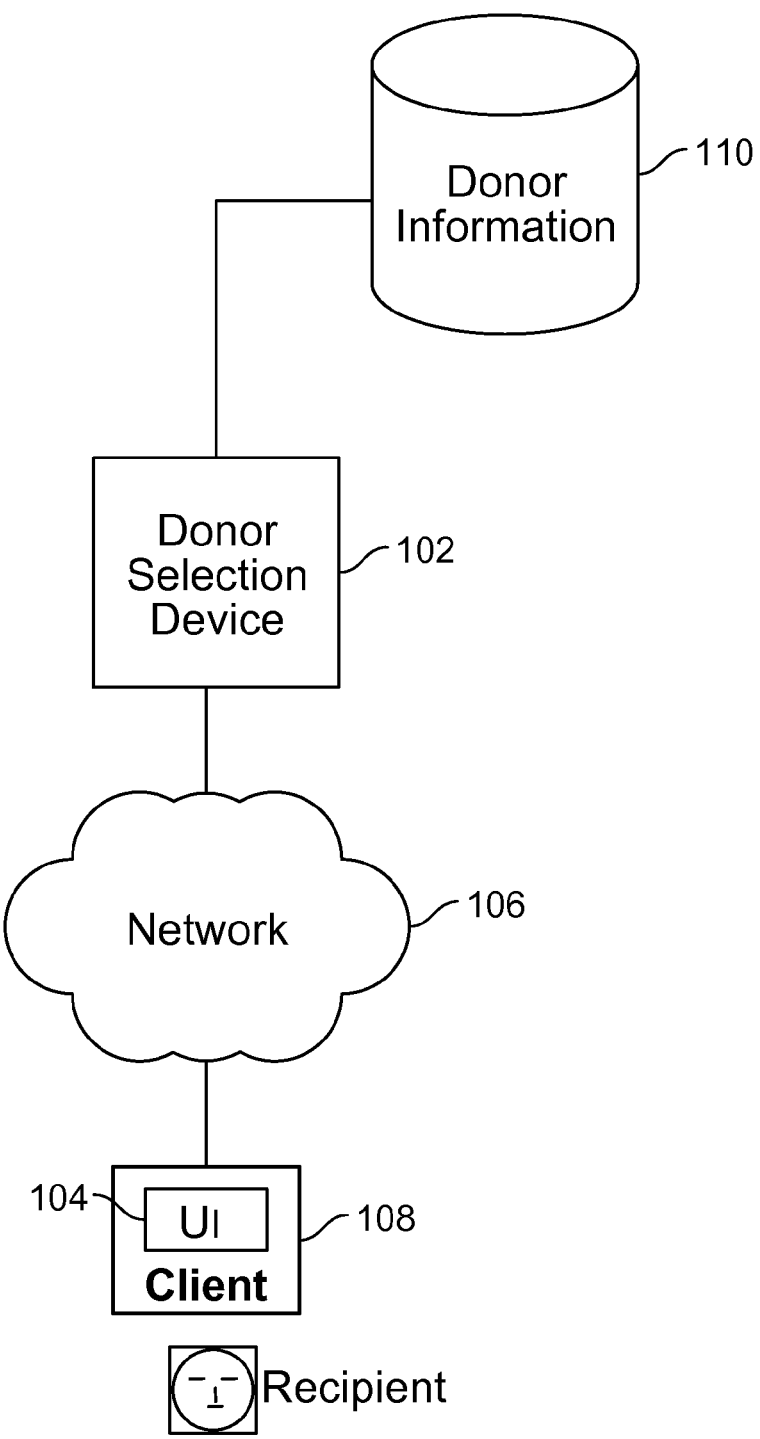
FIG. 1 is a block diagram illustrating an embodiment of a donor selection system.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Gamete donor selection based on genetic calculations is described. The gamete donors and gamete recipient's genetic information such as genome sequences and/or marker information is obtained and stored. In some embodiments, the recipient is allowed to make a specification of one or more phenotypes of interest in the hypothetical offspring. Statistical information pertaining to the likelihood of observing phenotypes of interest are determined, based on the genotype of the recipient and the genotypes of different donors. For example, probabilities of the phenotypes of interest in the hypothetical offspring resulting from different recipient-donor combinations are computed. Based on the statistical information, one or more preferred donors are identified and optionally selected by the recipient. In some embodiments, the recipient is allowed to make further inquiries about additional phenotypes in the hypothetical offspring with a particular selected donor.

As used herein, a phenotype refers to certain observable characteristic or trait of an organism, such as morphological, developmental, biochemical, physiological, or behavioral properties. Height, eye color, gender, personality characteristics and risk of developing certain types of cancer are examples of phenotypes. As used herein, genotype refers to information pertaining to the genetic constitution of a cell, an organism, or an individual in reference to a specific character under consideration, for example, information pertaining to a combination of alleles located on homologous chromosomes that is associated with a specific characteristic or trait.

FIG. 1 is a block diagram illustrating an embodiment of a donor selection system. Donor selection device 102 may be implemented using a server computer with one or more processors, a stand-alone computing device such as a desktop computer, a mobile device, specialized hardware device designed for implementing the donor selection process, or any other appropriate hardware, software, or combinations thereof. The operations of the donor selection device are described in greater detail below. In this example, a potential gamete recipient (or some other user such as the recipient's agent or a system operator) accesses the donor selection device via a network 106 using a client device 108 that provides a donor selection user interface 104. Alternatively, the recipient can access the donor selection device directly, for example by using software executing on the donor selection device, without requiring communication over a network. Information (including genetic information and optionally other personal information such as familial and environmental data) pertaining to the potential donors and the recipient is stored in a database 110, which can be implemented on an integral storage component of the donor selection device, an attached storage device, a separate storage device accessible by the donor selection device, or a combination thereof. Many different arrangements of the physical components are possible in various embodiments. In various embodiments, the entire genome sequences and/or specific markers (e.g., Single-Nucleotide Polymorphisms (SNPs), which are points along the genome with two or more common variations, Copy-Number Variations (CNVs), which are inserted or deleted lengths of DNA, etc.) are stored in the database to facilitate donor selection.

The recipient may specify certain phenotypes the recipient desires in his/her hypothetical offspring and send the specification to the donor selection device. As will be described in greater detail below, based on the genotype information of the donors and the recipient, the donor selection device performs inheritance calculations pertaining to the phenotypes of interest and identifies one or more preferred donors for the recipient.

Figure 2A:
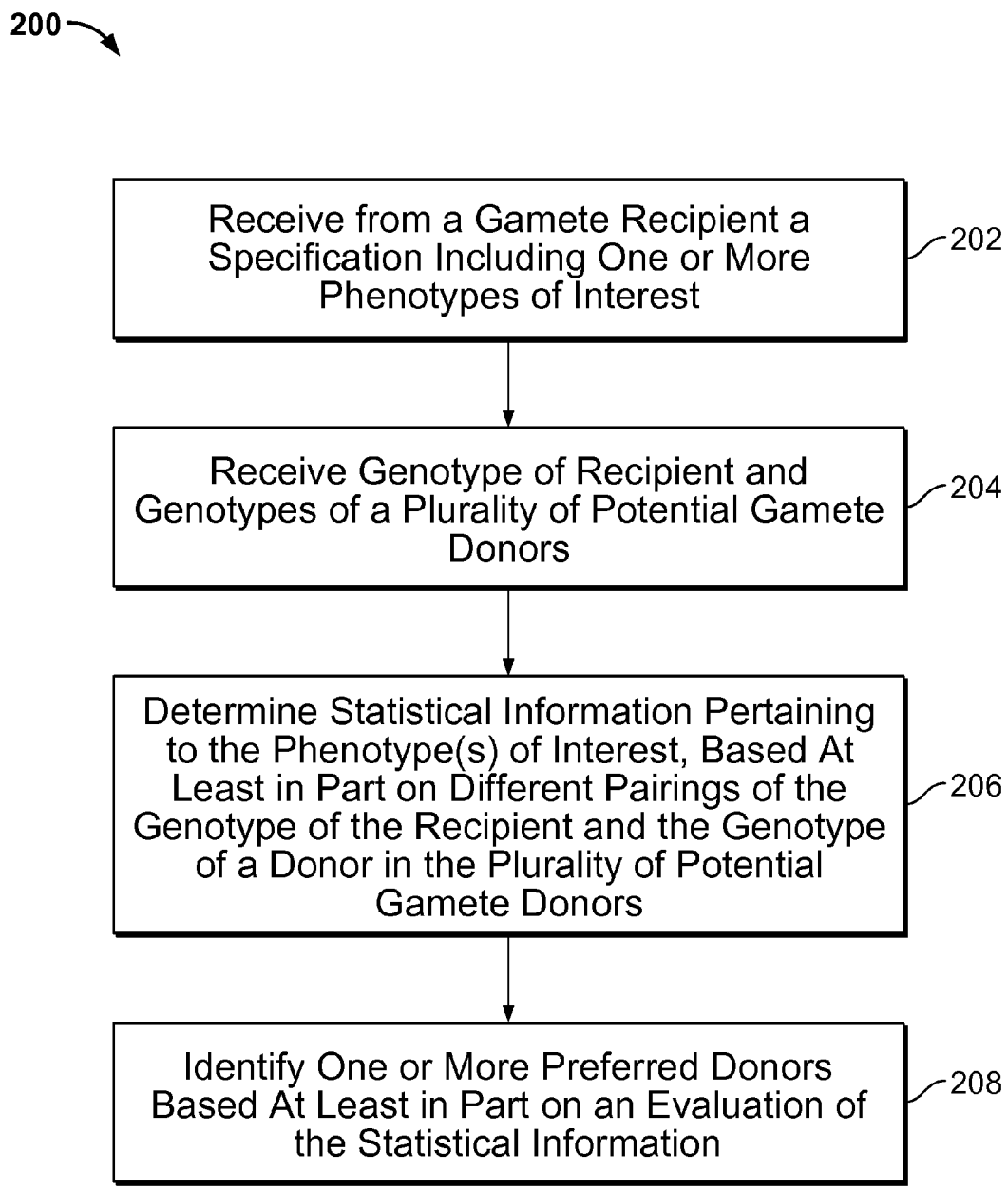
FIG. 2A is a flowchart illustrating an embodiment of a process for selecting a preferred donor.

FIG. 2A is a flowchart illustrating an embodiment of a process for selecting a preferred donor. Process 200 may be implemented on a donor selection device such as 102 of FIG. 1. The process initiates at 202. A specification including one or more phenotypes in a hypothetical child is received from a recipient. In some embodiments, the system is configured with a set of available phenotypes from which the recipient selects the set of phenotypes of interest. Various types of phenotypes such as physical traits (e.g., height, weight, eye color, etc.)

and inherited diseases (e.g., certain types of cancer, congenital heart defects, deafness, etc.) are provided through a user-selectable interface. The recipient's selection forms the specification. For example, the recipient may use user interface tools such as selection boxes to indicate that he/she desires an offspring who has the least likelihood of possessing a congenital heart defect, and has brown eyes. In some embodiments, the recipient is allowed to form a qualitative query in natural language, such as "which donors in this database, were their genetic material combined with mine, would be most likely to yield a child who will have colorectal cancer risk less than its parents, green eyes, and to have less than a 0.01% chance of a congenital heart defect?" The natural language query is parsed to form the specification. In some embodiments, the recipient may also express his or her preferences, for example "I prefer low risk of colorectal cancer and congenital heart defects and I prefer green eyes to other colors. The risks of colorectal cancer and heart defects are equally important to me, and are more important to me than eye color. Who are the most suitable donors in this database, subject to these preferences?" In some embodiments, the recipient is allowed to make a general specification such as the longest expected life span, the expected lifetime cost of healthcare, the expected lifetime cumulative duration of hospitalization, etc. The general specification is implemented as a combination of various specific phenotypes in some embodiments and as a single genotype influenced by multiple genotypes in other embodiments.

At 204, the genotype of the recipient and the genotypes of a number of gamete donors are received. The genotype information is received from a database in this example. In some embodiments, the genotypes retrieved in a batch. In some embodiments, the genotypes are received in multiple steps individually or in groups.

At 206, statistical information on the likelihood of the specified phenotype(s) is determined based at least in part on different pairings of the recipient's and a donor's genotype. In each pairing, the recipient's genotype is paired with a different donor's genotype. A phenotype may be affected by one or more markers in the genome. In some embodiments, for each phenotype, the affecting phenotype markers in the recipient and each donor are paired, probabilities of allowable permutations in the hypothetical offspring are evaluated, and the results are stored. For example, if a general specification was made by the recipient, genotypes determined to correspond to the specification are evaluated and the resulting statistical information pertaining to each genotype is evaluated and combined. For example, if the specification is the longest expected life span, then markers known to be associated with longevity (based on previous studies, etc.) may be employed; if the specification is the least expected lifetime cost of health care, then markers known to be associated with chronic diseases and/or diseases with expensive treatments may be employed; if the specification is the least expected lifetime cumulative duration of hospitalization, then markers known to be associated with diseases requiring hospitalization may be employed. The probability distributions associated with these markers are weight adjusted as appropriate to produce a combined score for each recipient-donor pair. The processing may be done serially or in parallel. In some embodiments, the results are cached and/or indexed to improve efficiency.

At 206, one or more preferred gamete donors are identified based at least in part on an evaluation of the statistical information. In some embodiments, the statistical distributions of the phenotypes resulting from different recipient-donor pairings and/or scores derived based on the statistical distributions are sorted and one or more high-ranking donors are identified. In some embodiments, the best donor/donors for each desired phenotype is/are identified and information such as donor's personal information and the probability that a hypothetical child will have the phenotype is presented to the recipient. In some embodiments where the recipient has indicated preferences with respect to certain phenotypes, the results for each phenotype calculation may be weighed to yield the preferred donor. For example, if the recipient has indicated that low probability of congenital heart defects is more important than brown eyes, then, depending on the weight assigned to each phenotype, a donor who would result in a hypothetical child who will have 0.1% chance of congenital heart failure and 70% chance of having brown eyes may be ranked higher than another donor who would result in 0.2% chance of congenital heart failure and 95% chance of having brown eyes in some cases, but lower in other cases. In some embodiments where the recipient has made a general specification that results in a measurement or score combining the available genotype calculations, the measurement or score corresponding to each donor is ranked for donor selection.

Figure 2B:
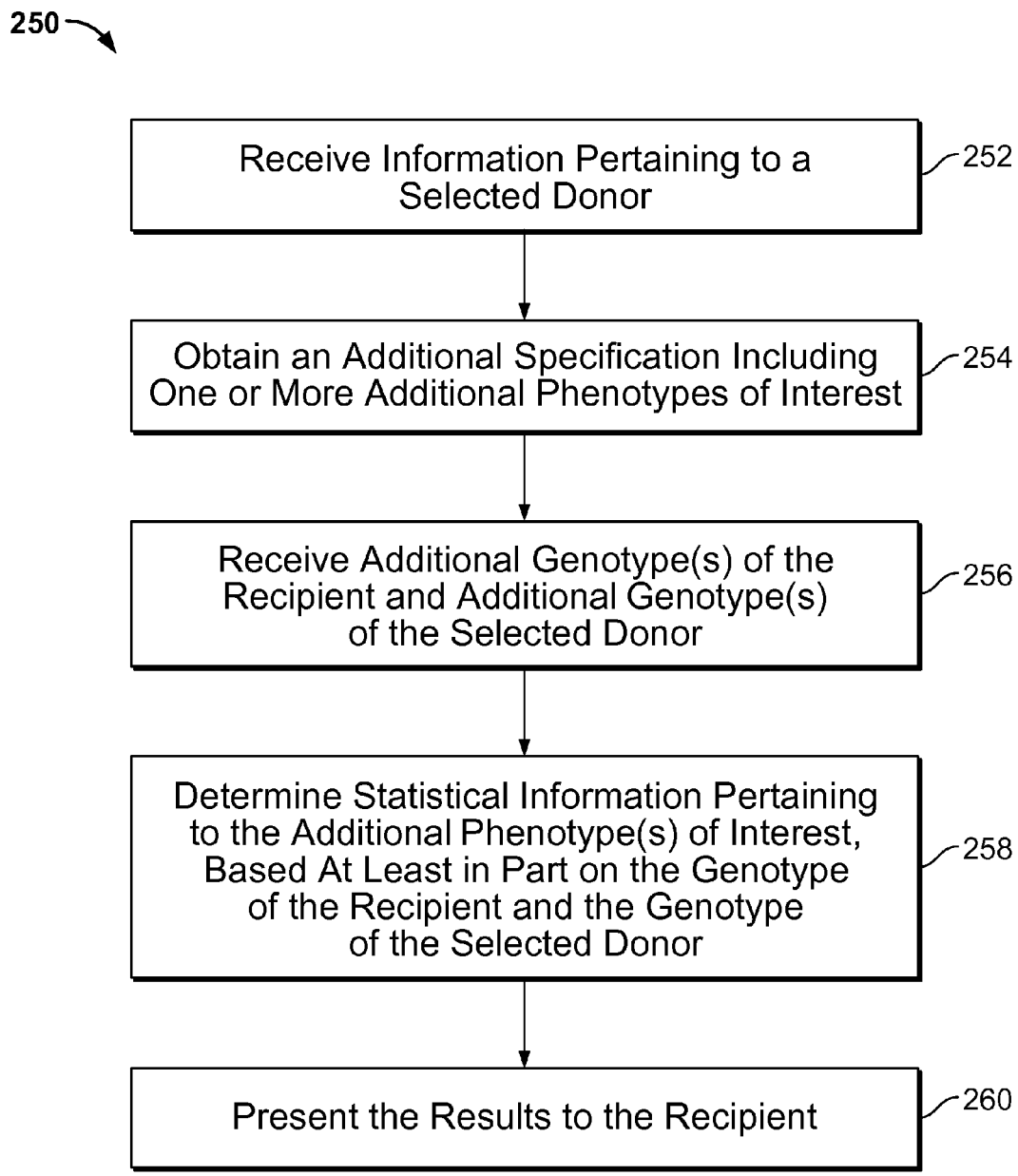
FIG. 2B is a flowchart illustrating an embodiment of a process for providing additional genetic counseling information to the recipient.

At this point, the recipient can make a donor choice and proceed with the fertilization process using the donor's gamete. Alternatively, the recipient has the option to obtain additional genetic counseling information pertaining to the hypothetical child with a selected donor. FIG. 2B is a flowchart illustrating an embodiment of a process for providing additional genetic counseling information to the recipient. Process 250 may be implemented on a donor selection device such as 102 of FIG. 1. The process starts at 252, where information pertaining to a selected donor, such as identification information and/or other information used to retrieve the donor's genetic data, is received. In some embodiments, the donor may be selected by the recipient from a list of preferred donors. In some embodiments, a single preferred donor (such as the top ranking donor) is selected by the system for the recipient. At 254, another specification including one or more additional phenotypes of interest is obtained. In some embodiments, the recipient inputs the specification in a way similar to 202 of process 200. In some embodiments, certain phenotypes are preconfigured by the system as phenotypes that may be of interest to the recipient. At 256, additional genotype(s)e of the recipient and additional genotype(s) of the selected donor are optionally received. In some embodiments, the information was already. previously obtained during process 200, and this step is therefore omitted. At 258, statistical information of the additional phenotype(s) is determined based on the genotype information of the recipient and the genotype information of the selected donor. At 260, the results are presented to the recipient.

The recipient may repeat process 200, process 250, or both to find a most suitable donor based on different phenotypes of interest.

Figure 3:
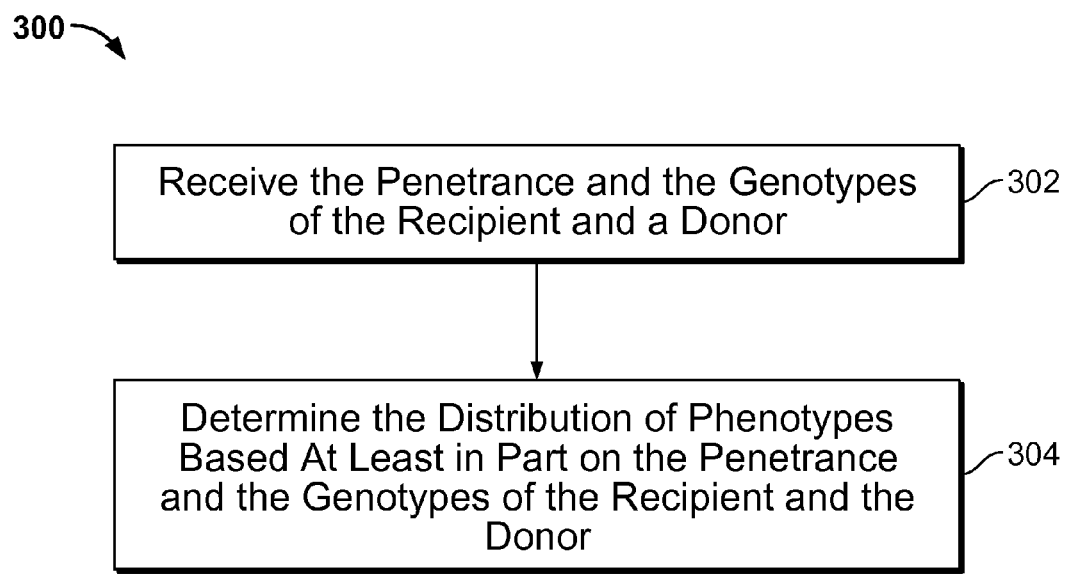
FIG. 3 is a flowchart illustrating an embodiment of a process for determining the statistical distribution of the phenotype of a hypothetical child resulting from the recipient's genotype and a donor's genotype.

FIG. 3 is a flowchart illustrating an embodiment of a process for determining the statistical distribution of the phenotype of a hypothetical child resulting from the recipient's genotype and a donor's genotype. Process 300 can be used to implement, for example, 206 of process 200 or 258 of process 250.

Several assumptions are made for calculating the statistical distribution. It is assumed that each individual is associated with a phenotype, denoted as $\phi$, which is a random variable. It is also assumed that each individual is associated with a genotype $G=(g_1, g_2, \ldots, g_n)$, where each $g_i$ is an unordered pair $(g_{i1}, g_{i2})$, and each $g_{ij}$ is a discrete-valued random variable. It is further assumed that the distribution over the possible values of $\phi$, conditional on the values of the individual's genotype, denoted as $Pr[\phi|G]$ (also known as the penetrance function), is available. The penetrance function is often determined through population studies and other empirical studies. It is typically considered as a property of a population group.

The statistical information of phenotypes from a recipient-donor combination is determined by calculating the probability of each phenotypic value of the hypothetical child of a prospective recipient and donor, having respective genotypes $G_R$ and $G_D$.

At 302, the value of the penetrance function (i.e., conditional distribution $Pr[\phi|G]$) and genotypes $G_R$ and $G_D$ are received. In some embodiments, this function and these data are obtained from a database.

At 304, the distribution of phenotypes in the hypothetical child conditioned on the hypothetical child's genotype, $G_C$, is computed based at least in part on the penetrance, and on the genotypes of the recipient and the donor.

In some embodiments, the calculation is as follows:

$$Pr[\phi=\phi_i|G_R, G_D] = \Sigma_{G_C \text{ in } G_R \square G_D} Pr[\phi=\phi_i|G_C] Pr[G_C|G_R, G_D]. \quad (1)$$

The operation $G_R \square G_D$ yields the set of all genotypes that may be produced by combining genotypes $G_R$ and $G_D$ according to the rules of genetic inheritance. As will be shown in greater detail below in connection with Example 1, the value of $Pr[G_C|G_R, G_D]$ is derived based on genetic principles in most cases. Other formulas are possible in other implementations.

In some embodiments, the possibilities of errors in the genotypes $G_R$ and $G_D$ are accounted in the calculation of the hypothetical child's genotypes. For example, if it is known that there is a chance $\delta$, $0<=\delta<=1$, that $G_R$ or $G_D$ may be incorrectly identified during the sequencing process, the calculated phenotype distribution in the hypothetical would be adjusted as follows:

$$Pr[\phi=\phi_i|G_R, G_D] = \Sigma_{G_R^* \text{ near } G_R} \Sigma_{G_D^* \text{ near } G_D} \Sigma_{G_C \text{ in } G_R \square G_D} Pr[\phi=\phi_i|G_C] Pr[G_C|G_R^*, G_D^*] Pr[G_R^*|G_R, \delta] Pr[G_D^*|G_D, \delta] \quad (2)$$

Here the set "$G_R^*$ near $G_R$" denotes genotypes $G_R^*$ that are in some neighborhood of the observed recipient genotype $G_R$. In this example, "neighborhood" refers to the set of genotypes that differ from $G_R$ at one SNP locus.

In some embodiments, information from the respective families of the recipient and donor is incorporated into the phenotype distribution calculations. The penetrance function is modified using the familial data. The modified penetrance function is $Pr[\phi|G, F]$, where F denotes familial data, as a list of the phenotypic values in close relatives of the recipient and/or donor, where "close" certainly includes relatives of the first- and second-degree, but may also include more distant relatives. The modified value may be based on population studies or other empirical data. For example, the penetrance function of having blue eyes given a genotype $G_0$, $Pr[\phi|G_0]$, without additional familial information, might have a value of 20%. With familial information that the recipient's (or donor's) parents also both have blue eyes, the value of the modified penetrance function $Pr[\phi|G_0, F]$ might instead have a value of 45%. Accordingly, the phenotype distribution calculation accounting for the familial data is as follows:

$$Pr[\phi=\phi_i|G_R, G_D, F] = \Sigma_{G_C \text{ in } G_R \square G_D} Pr[\phi=\phi_i|G_C, F] Pr[G_C|G_R, G_D]. \quad (3)$$

In some embodiments, information about the environment or behavior of the recipient, the donor and their families, such as smoking and body mass index, is incorporated into the phenotype calculation. The penetrance function is modified in such cases to the form $Pr[\phi|G, F, E]$, expressing the dependence of the hypothetical child's phenotype on environmental and behavioral data, represented by E, in addition to the genotype of the hypothetical child G and familial data F. The modified value may be based on population studies or other empirical data. For example, suppose that the occurrence of certain cardiovascular disease for a certain genotype, $Pr[\phi|G]$, is 30%. Given that the donor is a smoker and has a family history of the disease, the modified penetrance function $Pr[\phi|G, F, E]$ may be as high as 90%. Accordingly, the phenotype distribution calculation accounting for the environmental data is as follows:

$$Pr[\phi=\phi_i|G_R, G_D, F, E] = \Sigma_{G_C \text{ in } G_R \square G_D} Pr[\phi=\phi_i|G_C, F, E] Pr[G_C|G_R, G_D]. \quad (4)$$

In some embodiments, the phenotypes specified by the recipient are not independent. For example, skin color and hair color are non-independent phenotypes. Non independent phenotypes may occur because the phenotypes are influenced, at least in part, by the same genetic marker or markers. Non-independence may also occur because the phenotypes depend on genetic markers that are located near one another in the genome. Non-independence, such as that between height and weight, may also be caused by non-genetic factors, such as developmental or environmental factors that influence the phenotypes separately from the genotype or in interaction with the genotype. In some embodiments, the non-independent phenotypes are represented using a vector $\phi$ with joint phenotypes (for example, $\phi$=[height, weight]). The phenotype distribution calculation accounting for non-independent phenotypes is as follows:

$$Pr[\phi=(\phi_i,\phi_j)|G_R, G_D] = \Sigma_{GC\ in GR \square GD} Pr[\phi=(\phi_i,\phi_j)|G_C] Pr[G_C|G_R, G_D].  \quad (5)$$

A number of examples are provided below for purposes of illustration. Although examples involving a small number of markers are discussed below for purposes of illustration, genotypes associated with greater number of markers are possible.

EXAMPLE 1:

In this example, the probability that a hypothetical child will be able to perceive bitter flavors is calculated. About 25% of people are unable to taste a chemical called propylthiouracil (PROP) similar to the bitter components found in cabbage, raw broccoli, coffee, tonic water, and dark beers. These people are considered "taste-blind"—and compared to those who do respond to PROP, taste-blind people find most food and drink to be less bitter, or not bitter at all. Sensitivity to this kind of taste is due almost entirely to a single gene that encodes receptors in taste buds on the tongue. A SNP in this gene, whose identifier is rs713598, is responsible for whether a person is bitter taste-blind.

rs713598 has two alleles, C and G. In European-descended populations, the C allele has a frequency of about 40%, the G allele about 60%. The possible diploid genotypes for rs713598 are GG, CG, and CC.

Suppose that a recipient and a potential donor have respective rs713598 genotypes CG and CC. Based on equation (1) and its notations, the phenotype $\phi$ has two states, "Can Perceive Bitter Flavors", denoted $\phi_B$, and "Cannot Perceive Bitter Flavors", denoted $\phi_b$. Given that the recipient's genotype $G_R$ is (C, G), and the donor's genotype $G_D$ is (C, C), the operation $G_R \square G_D$ yields the set of possible hypothetical child genotypes {(C, C), (C, G)}. The function $Pr[G_C|G_R, G_D]$ follows the basic rules of inheritance, where the hypothetical child must receive a C allele from the recipient, and would receive a C or a G allele from the donor, each with probability of 50%. The probabilities are shown in the table below:

TABLE 1

| $G_C$ | $Pr[G_C|G_R, G_D]$ |
|---|---|
| (C, C) | 50% |
| (C, G) | 50% |

Those with the GG and CG genotypes can always taste bitter flavors, but only 20% of those with the CC genotype can taste bitter flavors. Thus, the penetrance function $Pr[\phi|G]$ has the following values:

TABLE 2

| $\phi_i$ | G | $Pr[\phi = \phi_i|G]$ |
|---|---|---|
| $\phi_B$ | (C, C) | 20% |
| $\phi_B$ | (C, G) | 100% |
| $\phi_B$ | (G, G) | 100% |
| $\phi_b$ | (C, C) | 80% |
| $\phi_b$ | (C, G) | 0% |
| $\phi_b$ | (G, G) | 0% |

The calculation of $Pr[\phi=\phi_B]$ and $Pr[\phi=\phi_b]$ for a hypothetical child resulting from the recipient and the donor is as follows:

$$Pr[\phi=\phi_B] = \Sigma_{GC\ in\ \{(C,C),(C,G)\}} Pr[\phi=\phi_B|G_C] Pr[G_C|G_M, G_D] = Pr[\phi=\phi_B|(C,C)] Pr[(C,C)|G_R, G_D] + Pr[\phi=\phi_B|(C,G)] Pr[(C,G)|G_R, G_D] = 20\% * \frac{1}{2} + 100\% * \frac{1}{2} = 60\%.$$

$$Pr[\phi=\phi_b] = Pr[\phi=\phi_b|(C,C)] Pr[(C,C)|G_R, G_D] + Pr[\phi=\phi_b|(C,G)|G_R, G_D] = 80\% * \frac{1}{2} + 0 * \frac{1}{2} = 40\%.$$

Thus, based on this recipient-donor combination, the probability that they produce a child that can taste bitter flavors is 60%, and the probability that they produce a child that cannot taste bitter flavors is 40%.

EXAMPLE 2:

In this example, the phenotype of age-related macular degeneration (AMD) is considered. AMD is the most common cause of irreversible vision loss in the Western world among people over 60. Three markers identified as rs1061147, rs547154, and rs3750847 are responsible for this disease. The wild type alleles, the risk alleles, and the occurrence frequency of the risk alleles associated with the SNPs are shown in the table below:

TABLE 3

| SNP | Wildtype Allele | Risk Allele | Risk Allele Frequency |
|---|---|---|---|
| rs1061147 | C | A | 0.392 |
| rs547154 | T | G | 0.937 |
| rs3750847 | C | T | 0.224 |

In this example, the recipient has (rs1061147, rs547154, rs3750847) genotype $G_R = ((A, C), (G, G), (C, C))$ and the donor has genotype $G_D = ((A, C), (G, G), (C, T))$. Using risk estimation techniques such as the techniques described in U.S. patent application Ser. No. 12/151,977 entitled "SUMMARIZING AN AGGREGATE CONTRIBUTION TO A CHARACTERISTIC FOR AN INDIVIDUAL," filed May 8, 2008, which is incorporated herein by reference for all purposes, it is estimated that that the lifetime risk of AMD in the recipient, $Pr[\phi=\phi_A|G_R]$, is 3.5%, and that the donor's risk, $Pr[\phi=\phi_A|G_D]$, is 11.3%, where the disease state is denoted as $\phi_A$, and the non-disease state as $\phi_a$.

In this case, the three SNPs are not located near one another and are independent of each other. As such, the probabilities of the possible genotypes in the hypothetical child are calculated from the basic rules of inheritance. In the table below are the six possible genotypes given these particular parental genotypes $G_R$ and $G_D$, their expected segregation frequencies, and the estimated risk of AMD, i.e. $Pr[\phi=\phi_A|G_C]$, for each genotype. Note that since both the recipient and the donor are homozygous for allele G at SNP rs547154, the only possible genotype they can produce at that that marker is GG.

TABLE 4

| rs1061147 Genotype | rs547154 Genotype | rs3750847 Genotype | Segregation Frequency | AMD Risk |
|---|---|---|---|---|
| AA | GG | CC | 12.5% | 9.5% |
| AC | GG | CC | 25% | 3.5% |
| CC | GG | CC | 12.5% | 1.3% |
| AA | GG | CT | 12.5% | 26.6% |
| AC | GG | CT | 25% | 11.3% |
| CC | GG | CT | 12.5% | 4.3% |

Based on the table, the probability that the hypothetical child will be afflicted with AMD, $Pr[\phi=\phi_A]$, is, according to equation (1):

(12.5%*9.5%)+(25%*3.5%)+(12.5%*1.3%)+(12.5%*26.6%)+
(25%*11.3%)+(12.5%*4.3%)=8.9%.

EXAMPLE 3

This example illustrates the problem of non-independent phenotypes. For this example, it is assumed that for a certain population group, heart disease occurs in 20% of those with an AA genotype at a given marker, and type 2 diabetes occurs in 30% of those with the AA genotype. Were the phenotypes independent, one would expect heart disease and diabetes to covary multiplicatively as follows:

TABLE 5

|  | No Heart Disease | Heart Disease |
| --- | --- | --- |
| No Diabetes | 56% | 14% |
| Diabetes | 24% | 6% |

As used herein, "covary multiplicatively" means that the expected frequency of a combination of phenotypes is the product of the individual probabilities. For example, if the phenotypes are truly independent, one would expect people to simultaneously suffer from both heart disease and diabetes at a frequency of 20% *30%=6%, as in the lower right cell. Suppose, however, that it is empirically observed that the joint phenotype frequencies within those who have the AA genotype are as follows:

TABLE 7

|  | No Heart Disease | Heart Disease |
| --- | --- | --- |
| No Diabetes | 63.7% | 6.3% |
| Diabetes | 16.3% | 13.7% |

Note that this table yields the correct marginal assessments; the column sums are 80% (=63.7%+16.3%) and 20% (=6.3%+13.7%), the row sums are 70% (=63.7%+6.3%) and 30% (=16.3%+13.7%), giving the correct marginal risks of 20% and 30%, respectively, as above.

Now suppose that a prospective recipient has genotype of AA at this marker, and is considering a donor with the same AA genotype. The assumption of independence would lead to an incorrect assessment for the joint heart disease and diabetes phenotype (of 6%). The correct estimate of 13.7% could only be given in the presence of the correct joint penetrance function, as provided for in this system.

In some embodiments, the donor list is pre-processed or post-processed to eliminate any donor that is found to be a close relative of the recipient. The degree of relatedness is configurable. For example, some system may be configured to exclude donors that are second cousins or closer relatives of the recipient, and some may be configured to exclude third cousins or closer. Various genealogical techniques, including those based on genetic information (such as DNA matching) and those based on non-genetic information (such as family tree information) may be used for determining how closely related the donor is to the recipient.

Once the phenotype distributions are computed for individual donors, the results are presented to the recipient. Depending on the recipient's specification and system implementation, the results may be presented in different ways.

FIG. 4 is a diagram illustrating an embodiment of a user interface for making user specification and displaying the results. In this example, the recipient has specified that she prefers low risk of colorectal cancer and congenital heart defects equally, and to a lesser degree she also prefers green eye color. A donor selection process such as 200 is performed, and the results page shows preferred donors A, B, and C. For each donor, the statistical distributions of the desired genotypes of the hypothetical child resulting from the combinations of the recipient and the donor, as well as an optional score calculated based on the statistical distribution are displayed. Alternatively, all the donors can be shown in a ranked list.

FIG. 5 is a user interface diagram illustrating another embodiment of a user interface that displays the results. In this example, the recipient has specified generally that she prefers the longest expected life span. The results page shows preferred donors X, Y, and Z, and the corresponding expected life span calculated for the hypothetical child resulting from each recipient-donor pair. Alternatively, all the donors can be shown in a ranked list.

Figure 6:
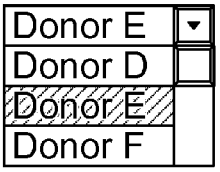
FIG. 6 is a diagram illustrating an embodiment of a user interface that allows the recipient to view additional traits.

In some embodiments, statistical distributions of various phenotypes in addition to the ones specified by the recipient are computed for one or more selected donors. FIG. 6 is a diagram illustrating an embodiment of a user interface that allows the recipient to view additional traits. In this example, it is assumed that donors D, E, and F are the preferred donors previously identified using a process such as 200. The system allows the recipient R to select a donor and view other possible phenotype of the hypothetical child resulting from the recipient's and the donor's gametes, such as alcohol flush reaction, lactose tolerance, muscle performance, and any other appropriate phenotype that may be determined using a process similar to process 250. The genotypes of the recipient and the selected donor are displayed. The probabilities of observing these specific genotypes in the offspring are also calculated and displayed.

Gamete donor selection based on genetic computations has been disclosed. The technique allows the potential gamete recipients to make more informed donor choices.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for gamete donor selection comprising:
   one or more processors configured to:
      receive a specification including a phenotype of interest that can be present in a hypothetical offspring;
      receive a genotype of a recipient and a plurality of genotypes of a respective plurality of donors;
      determine statistical information including probabilities of observing the phenotype of interest resulting from different combinations of the genotype of the recipient and genotypes of the plurality of donors; and
      identify a preferred donor among the plurality of donors, based at least in part on an evaluation of the statistical information determined, including:
         to compare the probabilities of observing the phenotype of interest resulting from different combinations of the genotype of the recipient and the genotypes of the plurality of donors to identify the preferred donor; and
   a memory coupled to the processor, configured to provide the processor with instructions.

2. The system of claim 1, further comprising a database coupled to the processor, configured to store the genotypes of the plurality of donors.

3. The system of claim 1, wherein to determine the statistical information includes to compute the probabilities of observing the phenotype of interest resulting from different combinations of the genotype of the recipient and genotypes of the plurality of donor based at least in part on a penetrance function that is a distribution of possible phenotypes conditional on an input genotype.

4. The system of claim 3, wherein to determine the statistical information includes to modify the penetrance function to include possibility of errors in the genotype of the recipient, possibility of errors in the genotype of the donor, or both.

5. The system of claim 3, wherein to determine the statistical information includes to modify the penetrance function to include familial data of the recipient, familial data of the donor, or both.

6. The system of claim 3, wherein to determine the statistical information includes to modify the penetrance function to include environmental data of the recipient, environmental data of the donor, or both.

7. The system of claim 3, wherein:
the specification includes a plurality of non-independent phenotypes that depend on at least one shared genetic marker, depend on genetic markers that are located near one another in the genome, and/or depend non-genetic factors; and
to determine the statistical information includes to modify the penetrance function to represent the plurality of non-independent phenotypes as a joint phenotype.

8. The system of claim 1, wherein the processor is further configured to identify any donor that is deemed to be a close relative of the recipient.

9. The system of claim 1, wherein the processor is further configured to:
receive an additional specification that includes an additional phenotype of interest;
determine additional statistical information including probabilities of observing the additional phenotype of interest resulting from different combinations of an additional genotype of the recipient and an additional genotype of the preferred donor, including to:
compute the probabilities of observing the additional phenotype of interest resulting from different combinations of the genotype of the recipient and genotypes of the plurality of donor based at least in part on a penetrance function that is a distribution of possible phenotypes conditional on an input genotype.

10. The system of claim 9, wherein the processor is further configured to supply display information for displaying the additional statistical information.

11. A method for gamete donor selection, comprising:
receiving a specification including a phenotype of interest that can be present in a hypothetical offspring;
receiving a genotype of a recipient and a plurality of genotypes of a respective plurality of donors;
using one or more computer processors coupled to one or more memories configured to provide the one or more computer processors with instructions to determine statistical information including probabilities of observing the phenotype of interest resulting from different combinations of the genotype of the recipient and genotypes of the plurality of donors; and
identifying a preferred donor among the plurality of donors, based at least in part on the statistical information determined, including:
comparing the probabilities of observing the phenotype of interest resulting from different combinations of the genotype of the recipient and the genotypes of the plurality of donors to identify the preferred donor.

12. The method of claim 11, further comprising storing the genotypes of the plurality of donors.

13. The method of claim 11, wherein determining the statistical information of the phenotype includes computing the probabilities of observing the phenotype of interest resulting from different combinations of the genotype of the recipient and genotypes of the plurality of donor based at least in part on a penetrance function that is a distribution of possible phenotypes conditional on an input genotype.

14. The method of claim 13, wherein determining the statistical information includes modifying the penetrance function to include possibility of errors in the genotype of the recipient, possibility of errors in the genotype of the donor, or both.

15. The method of claim 13, wherein determining the statistical information includes modifying the penetrance function to include familial data of the recipient, familial data of the donor, or both.

16. The method of claim 13, wherein determining the statistical information includes modifying the penetrance function to include environmental data of the recipient, environmental data of the donor, or both.

17. The method of claim 13, wherein:
the specification includes a plurality of non-independent phenotypes that depend on at least one shared genetic marker, depend on genetic markers that are located near one another in the genome, and/or depend non-genetic factors; and
determining the statistical information includes modifying the penetrance function to represent the plurality of non-independent phenotypes as a joint phenotype.

18. The method of claim 11, further comprising excluding any donor that is deemed to be a close relative of the recipient.

19. The method of claim 11, wherein further comprising:
receiving an additional specification that includes an additional phenotype of interest; and
determining additional statistical information including probabilities of observing the additional phenotype of interest resulting from different combinations of an additional genotype of the recipient and an additional genotype of the preferred donor, including:
computing the probabilities of observing the additional phenotype of interest resulting from different combinations of the genotype of the recipient and genotypes of the plurality of donor based at least in part on a penetrance function that is a distribution of possible phenotypes conditional on an input genotype.

20. The method of claim 19, further comprising displaying the additional statistical information.

21. A non-transitory computer program product for gamete donor selection, the computer program product being embodied in a computer readable storage medium and comprising computer instructions for:
receiving a specification including a phenotype of interest that can be present in a hypothetical offspring;
receiving a genotype of a recipient and a plurality of genotypes of a respective plurality of donors;
determining statistical information including probabilities of observing the phenotype of interest resulting from different combinations of the genotype of the recipient and genotypes of the plurality of donors; and
identifying a preferred donor among the plurality of donors, based at least in part on an evaluation of the statistical information determined, including:

comparing the probabilities of observing the phenotype of interest resulting from different combinations of the genotype of the recipient and the genotypes of the plurality of donors to identify the preferred donor.

22. The system of claim 1, wherein to identify a preferred donor comprises to rank the probabilities of observing the phenotype of interest resulting from different combinations of the genotype of the recipient and the genotypes of the plurality of donors.

23. The method of claim 11, wherein identifying a preferred donor comprises ranking the probabilities of observing the phenotype of interest resulting from different combinations of the genotype of the recipient and the genotypes of the plurality of donors.

24. The non-transitory computer program product of claim 21, further comprising computer instructions for storing the genotypes of the plurality of donors.

25. The non-transitory computer program product of claim 21, wherein determining the statistical information of the phenotype includes computing the probabilities of observing the phenotype of interest resulting from different combinations of the genotype of the recipient and genotypes of the plurality of donor based at least in part on a penetrance function that is a distribution of possible phenotypes conditional on an input genotype.

26. The non-transitory computer program product of claim 21, further comprising computer instructions excluding any donor that is deemed to be a close relative of the recipient.

27. The non-transitory computer program product of claim 21, further comprising computer instructions for:
receiving an additional specification that includes an additional phenotype of interest; and
determining additional statistical information including probabilities of observing the additional phenotype of interest resulting from different combinations of an additional genotype of the recipient and an additional genotype of the preferred donor, including:
computing the probabilities of observing the additional phenotype of interest resulting from different combinations of the genotype of the recipient and genotypes of the plurality of donor based at least in part on a penetrance function that is a distribution of possible phenotypes conditional on an input genotype.

28. The non-transitory computer program product of claim 21, wherein identifying a preferred donor comprises ranking the probabilities of observing the phenotype of interest resulting from different combinations of the genotype of the recipient and the genotypes of the plurality of donors.

* * * * *